RHODODENDRON PLANT
Filed June 26, 1974
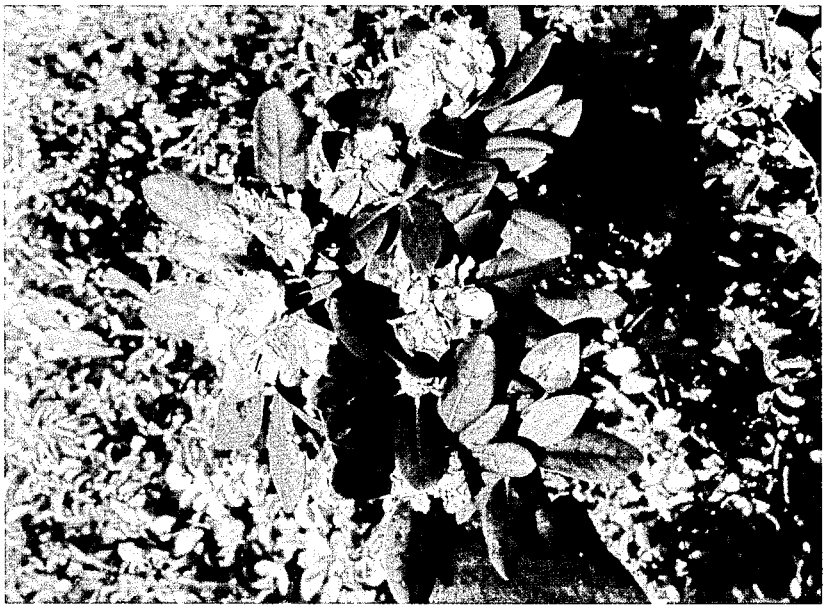
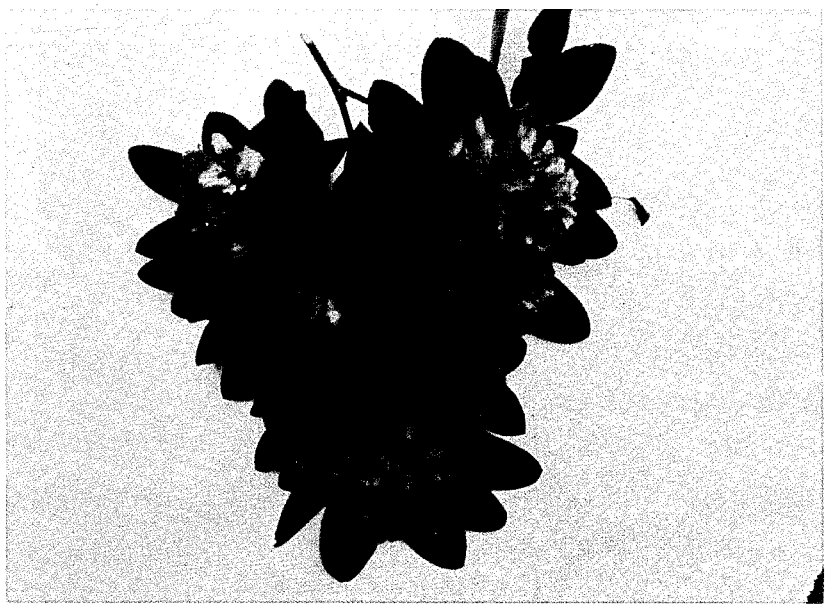

United States Patent

Plant Pat. 3,900

Patented June 1, 1976

3,900

RHODODENDRON PLANT

John Kraynak, Sr., John Kraynak, Jr., and George A. Kraynak, Sharon, Pa., assignors to Kraynak's, Inc., Sharon, Pa.

Filed June 26, 1974, Ser. No. 483,388

Int. Cl. A01h *5/00*

U.S. Cl. Plt.—55 1 Claim

This invention pertains to a new and distinct variety of rhododendron characterized particularly by the blooming periods of the plant.

This new variety was discovered growing as a chance seedling in a bed of rhododendrons grown in the nursery of petitioners in Sharon, Pa. Neither the pollen plant nor the seed parent of this new variety is known. The plant has been asexually propagated by cuttings in petitioners' greenhouses, and all descendants have shown the same characteristics, which illustrates that the descendants are true and that this new variety has become established.

This new variety of rhododendron, when grown in the region of Sharon, Pa., will begin to put forth buds in July, and the plant will then begin to bloom in the following September and bloom into October, weather conditions permitting. This characteristic has been observed for approximately 10 years.

The new and distinct variety of rhododendron plant, characterized particularly as to novelty: by its regular yearly fall season flowering from about 40% of the flower buds, without subsequent winter injury to the remainder of the flower buds which open midseason the following spring season; enlarged green basal bud scales about ¾ inches long; ease of propagation; restrained rate of growth (24–30″ after 5 years); convex leaves about 3 and ⅝ inches by 1 and ⅞ inches; R.H.S. yellow-green group 146A, with a thin line of dark brown tomentum on either side of the nether mid-rib; and bud hardness to minus seventeen degrees Fahrenheit. Florets are about 1½ inches diameter, R.H.S. purple group 75C, edged purple group 78B, with sparse ochre spotting on the dorsal lobe, ten to a truss; 10 stamens, the filaments of which are the same color as the interior of the flower; style lavender, shading red at the distal end, with a red stigma; calyx minute, nearly white; pedicels ⅝ inches long, nearly white; foliage moderately dense. The plant is grown from open-pollinated seed, so the parentage is unknown. Asexually propagated plants display the same characteristics as the original seedling.

An identification of the color of the bloom as by reference to the Royal Historical Society color chart is Red-Purple group, Card Number 74, Color Range D on card.

Having thus described our invention, what we claim is new and desire to secure by Plant Letters Patent of the United States is:

1. A new and distinct variety of rhododendron plant, substantially as shown and described, characterized by the distinctive color of its flower and foliage, and by its multiple blooming periods.

No references cited.

ROBERT E. BAGWILL, Primary Examiner